(12) United States Patent
Hahn

(10) Patent No.: US 9,393,036 B2
(45) Date of Patent: Jul. 19, 2016

(54) MANIPULATOR WITH GUIDING INSERT

(75) Inventor: Martin Hahn, Boll (DE)

(73) Assignee: Karl Storz GmbH & Co. KG (DE)

( * ) Notice: Subject to any disclaimer, the term of this patent is extended or adjusted under 35 U.S.C. 154(b) by 788 days.

(21) Appl. No.: 12/784,128

(22) Filed: May 20, 2010

(65) Prior Publication Data

US 2010/0298633 A1    Nov. 25, 2010

(30) Foreign Application Priority Data

May 20, 2009   (DE) .......................... 10 2009 022 119

(51) Int. Cl.
| | | |
|---|---|---|
| *A61B 17/00* | (2006.01) | |
| *A61B 17/29* | (2006.01) | |
| *F16C 1/20* | (2006.01) | |
| *A61B 17/16* | (2006.01) | |

(52) U.S. Cl.
CPC . *A61B 17/29* (2013.01); *F16C 1/20* (2013.01); *A61B 17/1611* (2013.01); *A61B 2017/00845* (2013.01); *A61B 2017/2901* (2013.01); *A61B 2017/2902* (2013.01); *A61B 2017/2904* (2013.01); *A61B 2217/005* (2013.01)

(58) Field of Classification Search
CPC ..................................................... A61B 19/22
USPC ............................................................ 606/1
See application file for complete search history.

(56) References Cited

U.S. PATENT DOCUMENTS

| | | | |
|---|---|---|---|
| 4,580,551 A | | 4/1986 | Siegmund et al. |
| 4,911,148 A | | 3/1990 | Sosnowski et al. |
| 5,314,424 A | * | 5/1994 | Nicholas .................... 606/41 |
| 6,139,563 A | * | 10/2000 | Cosgrove et al. ............. 606/205 |
| 6,585,717 B1 | | 7/2003 | Wittenberger et al. |
| 7,147,650 B2 | * | 12/2006 | Lee ............................. 606/205 |
| 7,686,826 B2 | * | 3/2010 | Lee et al. .................... 606/205 |
| 2002/0026145 A1 | * | 2/2002 | Bagaoisan et al. ......... 604/96.01 |
| 2003/0036748 A1 | * | 2/2003 | Cooper et al. .................. 606/1 |
| 2004/0054355 A1 | * | 3/2004 | Gerbi et al. ..................... 606/1 |
| 2005/0143660 A1 | * | 6/2005 | Rabiner et al. ............... 600/467 |
| 2006/0020287 A1 | * | 1/2006 | Lee et al. ..................... 606/205 |
| 2006/0025749 A1 | * | 2/2006 | Moenning .................... 604/506 |
| 2006/0149316 A1 | * | 7/2006 | DeVries et al. .............. 606/205 |

FOREIGN PATENT DOCUMENTS

| | | |
|---|---|---|
| EP | 1055397 B1 | 5/2001 |
| EP | 1872729 B1 | 10/2009 |
| WO | 2008012146 A1 | 1/2008 |

* cited by examiner

*Primary Examiner* — William Thomson
*Assistant Examiner* — John R Downey
(74) *Attorney, Agent, or Firm* — Whitmyer IP Group LLC

(57) ABSTRACT

A manipulator includes a proximal end, a distal end with a manipulation device, a shaft between the proximal end and the distal end, and a transmission element for transmitting at least either a force or a motion between the proximal end and the distal end. Provided in the shaft is a guide insert for guiding the transmission element, such that the transmission element can slide with respect to the guide insert in the longitudinal direction of the shaft.

19 Claims, 3 Drawing Sheets

MANIPULATOR WITH GUIDING INSERT

CROSS-REFERENCE TO RELATED APPLICATIONS

The present application claims priority of German patent application No. 10 2009 022 119.0 filed on May 20, 2009.

FIELD OF THE INVENTION

The present invention relates to a manipulator, in particular an endoscopic manipulator, for medical or non-medical technical purposes.

BACKGROUND OF THE INVENTION

A manipulator, in particular an endoscopic manipulator for medical or non-medical technical applications, comprises, for instance, gripping members on a proximal end that can be slid, rotated, or pivoted with respect to one another and, on a distal end, a manipulation device. The distal end is connected with the proximal end by a rigid or flexible shaft. If the gripping members on the proximal end are moved with respect to one another and/or a force or moment acts on the gripping members, this motion and/or this force or this moment is transmitted to the manipulation device. For this purpose a transmission element, which can move with respect to the shaft, is provided in the shaft of the manipulator. If the shaft is bent or bendable, then at least either the shaft or the transmission element must be flexible, at least in areas in which the bending varies, in order to make a relative mobility possible.

In patent EP 1 055 397 A1, a medical instrument for severing tissue in the human or animal body is described in which a spiral spring surrounds a rigid bent rod and is slid with respect to said rod in order to transmit a force from the gripping members on one end of the instrument to a tool on the other end of the instrument.

In patent EP 1 872 729 A1, a medical element for gripping an object is described. A force transmission element with a helical structure is positioned in a shaft between a grip and a distal section.

The helical force transmission element described in patent EP 1 872 729 A1 must be bendable and thus must comprise an elastic material, for instance plastic. Consequently, however, the force transmission element also comprises a high pliability, or compressibility and stretchability, in the longitudinal direction, in which it is to transmit a force. In addition, the force transmission element comprises a surface of some size that is internally contiguous with the shaft. The resulting sliding friction or static friction makes sensitive operation difficult and increases wear and tear. The weakening of the cross-section of the force transmission element between the coils and turns of its helical structure is desirable to increase the flexibility. At the same time, however, because of the stress concentration there, it is particularly easy for fissures or other damage to occur in the force transmission element that can lead to its failure.

SUMMARY OF THE INVENTION

It is an object of the present invention to provide an improved manipulator.

This object is achieved as a result of the contents of the principal claims.

Refinements can be found in the subsidiary claims.

Various embodiments of the present invention are based on the concept of providing within the shaft of a manipulator a guide insert that guides a traction or compression rod as a transmission element. Because the traction or compression rod is guided by the guide insert, it can have a cross-section that is small and, at least partially, is constant or location-independent in the longitudinal direction. Because of the small cross-section, the traction or compression rod can be composed of steel or another material with a low elasticity. The traction or compression rod is therefore a transmission element with a clearly lower compressibility or stretchability than, for instance, the helical force transmission element described in patent EP 1 872 729 A 1.

Because of the possible small cross-section of the traction or compression rod or of the transmission element, the friction, in particular the static friction between the transmission element and the shaft or the guide insert in the shaft, is reduced. As a result, sensitive operation becomes possible with the manipulator. This is particularly advantageous for medical as well as other non-medical technical applications. Because of the reduced friction, wear and tear is also reduced.

The possible constant cross-section of the transmission element, in addition, reduces the risk of damage to the transmission element through fissures or in other ways, because in the absence of stress concentration no local maximum strains occur.

A manipulator includes a proximal end, a distal end with a manipulation device, a shaft between the proximal end and the distal end, and a transmission element for transmitting at least either a force or a motion between the proximal end and the distal end of the shaft. Provided in the shaft is a guide insert for guiding the transmission element, such that the transmission element can slide with respect to the guide insert in the longitudinal direction of the shaft.

The transmission element is in particular a traction or compression rod. The cross-section of the transmission element can be constant, or essentially constant, or essentially constant in some sections, between the proximal end and the distal end. The guide insert, in particular, comprises a concentric or eccentric channel in which the transmission element is slidably positioned.

To increase the flexibility of the guide insert, it can comprise alternating support sections and flexible sections in the longitudinal direction. The support sections are configured to be contiguous with the inner wall of the shaft. The flexible sections can, in particular, comprise a cross-section that is clearly reduced in proportion to the support sections. Alternatively or in addition, the flexible sections can comprise a material that is more elastic than a material of the support sections. The support sections can comprise irrigation openings through which an irrigation fluid can flow in the shaft's longitudinal direction. Alternatively to the alternating position of the support sections and the flexible sections, the guide insert can have a helical structure. If the guide insert comprises a channel for the transmission element, this channel can be positioned entirely inside the cross-section of the guide insert throughout the entire length of the guide insert or else only in sections.

The transmission element and the guide insert can be of two different materials. For instance, the transmission element can be stainless steel or another material with low elasticity, to ensure low compressibility or stretchability of the transmission element. The guide insert can, for instance, be made of polyetheretherketone (PEEK; an aromatic, partly crystalline thermoplast of the group of polyaryletherketones) or another polyaryletherketone (PAEK) or another thermoplast or PTFE (also known by the trade name Teflon).

The manipulator's shaft can be bent or bendable by virtue of its own elasticity or by means of joints. The manipulation device can comprise at least either a forceps or a gripping device or a cutting tool or punching tool. The manipulator is in particular an endoscopic manipulator for medical or non-medical technical applications.

A guide insert for a manipulator with a shaft between a proximal end and a distal end includes at least one section with a cross-section adapted to a hollow space of the shaft and a channel in which a transmission element can be slidably positioned for transmitting at least either a force or a motion between the proximal and the distal ends of the shaft. The guide insert can have the aforementioned properties.

The invention is applicable, for instance, for a uterine manipulator.

BRIEF DESCRIPTION OF THE DRAWINGS

Hereinafter, embodiments are further described with reference to the appended illustrations.

DETAILED DESCRIPTION OF THE INVENTION

Figure 1:
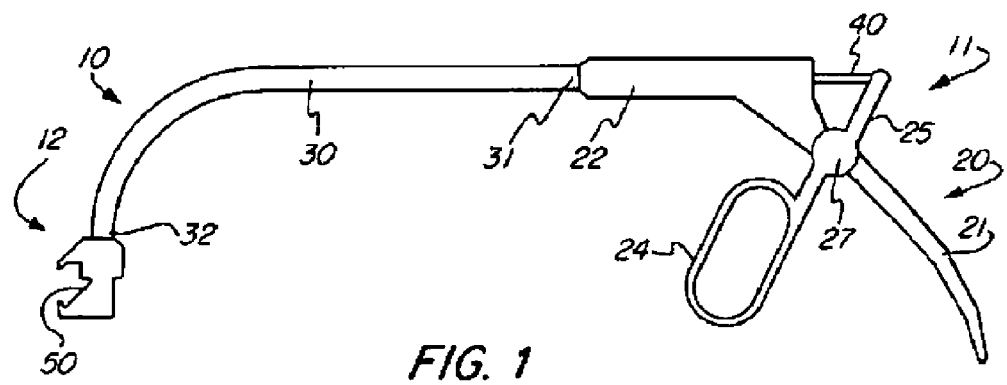
FIG. 1 is a schematic depiction of an endoscopic manipulator.

FIG. 1 is a schematic depiction of a manipulator 10, in particular of an endoscopic manipulator for medical or non-medical technical applications. The manipulator 10 includes a handling device 20 on a proximal end 11. The handling device 20 includes a fixed gripping member 21, a connection element 22, a movable gripping member 24, a lever 25, and a joint 27. The fixed gripping member 21 is rigidly connected with the connection element 22. The lever 25 is rigidly connected with the movable gripping member 24. The joint 27 connects the fixed gripping member 21 and the connection element 22, on the one hand, and the movable gripping member 24 and the lever 25, on the other hand, in such a way that the movable gripping member 24 and the lever 25 can rotate or pivot with respect to the fixed gripping member 21 and the connection element 22 around an axis that is perpendicular or essentially perpendicular to the visual plane of FIG. 1. The fixed gripping member 21 and the movable gripping member 24 are configured in such a way that a person can grip with one hand the fixed gripping member 21 and the movable gripping member 24, can therewith hold the handling device 20, guide the manipulator 10, and simultaneously move the fixed gripping member 21 and the movable gripping member 24 with respect to one another.

Alternatively, the movable gripping member can also be rotated with respect to the fixed gripping member in or around it or in some cases translationally pushed over bent or generally non-straight stretches with respect to the fixed gripping member.

The manipulator 10 further includes a shaft 30 with a proximal end 31 and a distal end 32. The proximal end 31 of the shaft 30 is connected with the connection element 22 of the handling device 20, in particular rigidly connected. The shaft 30 consists in particular of a tube, which can be rigid or at least flexible in certain sections.

The manipulator 10 also includes a transmission element 40, in particular in the form of a thin and at least in some sections flexible rod, which is positioned in the shaft 30. The transmission element 40 extends out of the connection element 22 on the proximal end 11 of the manipulator. The end of the transmission element 40 is in a jointed coupling there with the lever 25 of the handling device 20.

Figure 6:
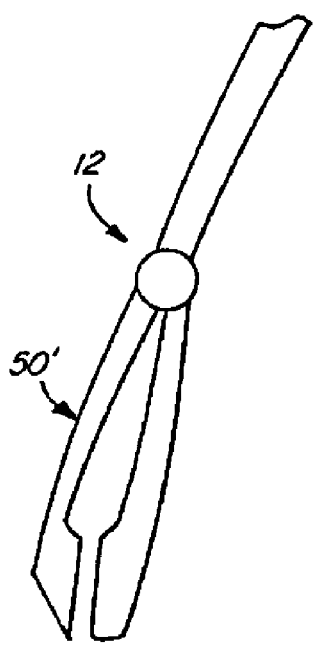
FIG. 6 is a schematic depiction of a forceps.
Figure 7:
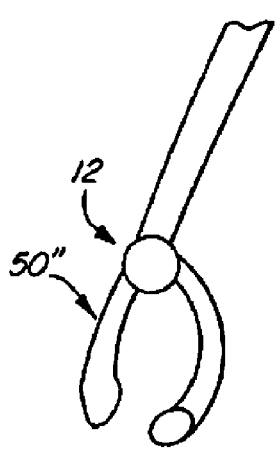
FIG. 7 is a schematic depiction of a grip.
Figure 8:
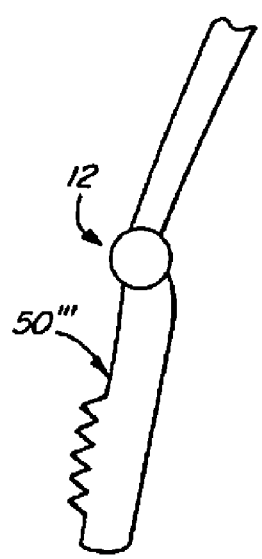
FIG. 8 is a schematic depiction of a cutting tool and punching tool.

The manipulator 10 also includes on its distal end 12 a manipulation device 50 that is connected with the distal end 32 of the shaft 30. The manipulation device 50 is, or includes, for instance a forceps or a grip or a cutting tool or punching tool or a spreading device or dilator. The manipulation device 50 is shown only schematically in FIG. 1. The forceps 50', grip 50" and cutting and punching tool 50''' are shown in FIGS. 6-8, respectively.

The transmission element 40 is connected or coupled, so that it can slide longitudinally in the shaft 30, on the proximal end 11 of the manipulator 10 with the lever 25 and on the distal end 12 of the manipulator 10 with the manipulation device 50. A relative motion of the movable gripping member 24 with respect to the fixed gripping member 21 is transmitted by means of a corresponding relative motion of the transmission element 40 with respect to the shaft 30 to the manipulation device 50. Correspondingly, a force is transmitted to the fixed gripping member 21 and the movable gripping member 24 or a reciprocal tensing of the fixed gripping member 21 and of the movable gripping member 24 by the shaft 30 and the transmission element 40 onto the manipulation device 50.

Figure 2:
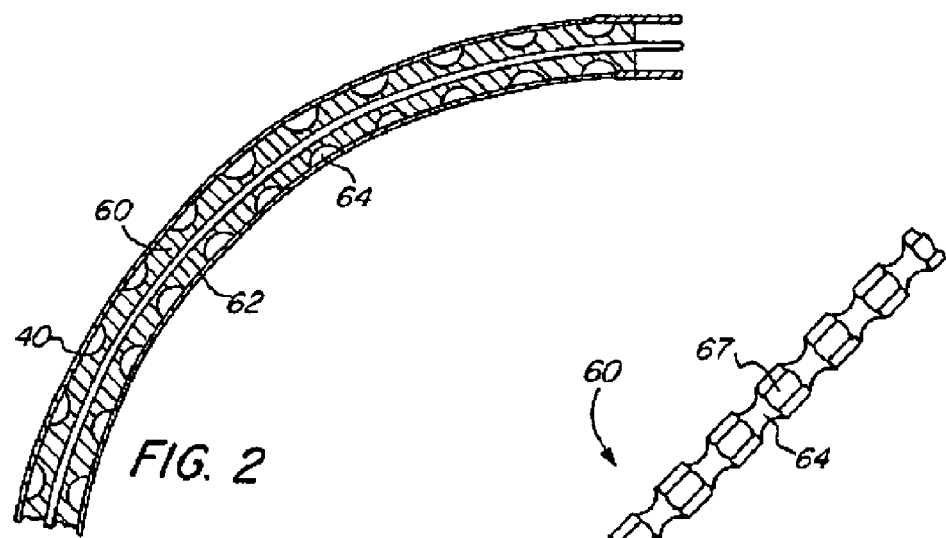
FIG. 2 is a schematic depiction of a partly sectioned shaft of a manipulator.

FIG. 2 is a schematic depiction of a longitudinal section of the shaft 30 in a bent area. The sectional plane is parallel to the visual plane of FIG. 1.

Positioned in the tubular shaft 30 is a guide insert 60, which is described more fully hereinafter with reference to FIG. 3. The transmission element 40 is positioned in the guide insert 60. The guide insert 60 comprises support sections 62 and flexible sections 64. The support sections 62 are contiguous with the interior wall of the tubular shaft 30. The flexible sections 64 have a reduced cross-section and allow a bending of the guide insert 60 corresponding to the bend of the shaft 30. Because of the smaller cross-section, the flexible sections 64 can be more easily reshaped elastically or else plastically than the support sections 62. Nevertheless the support sections 62 can also contribute to the bending elasticity of the guide insert 60.

The transmission element 40 is positioned in a channel 66. The channel 66 is, in particular, centered or in the middle of the cross-section of the guide insert 60. The cross-section of the channel 66 is adapted to the cross-section of the transmission element 40 in such a way that the transmission element 40 can be moved with little friction in the channel 66 in the longitudinal direction, on the one hand, and is guided in the transversal direction, on the other hand.

Figure 3:
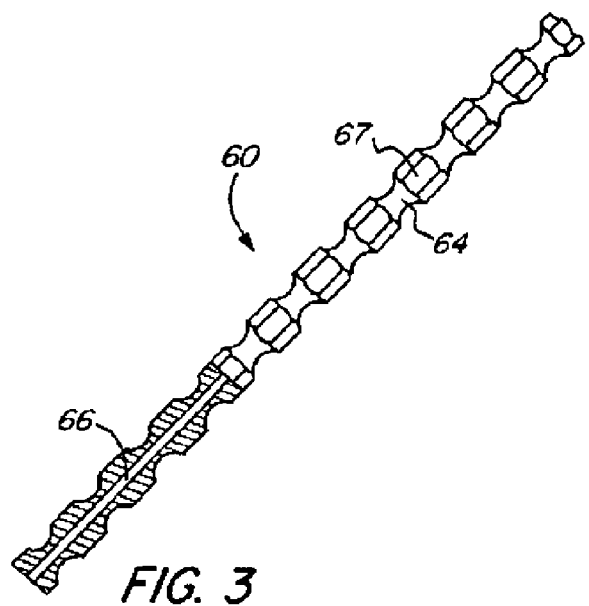
FIG. 3 is a schematic depiction of a guide insert.

FIG. 3 is a schematic depiction of the guide insert 60 already described with reference to the foregoing FIG. 2. Shown in the upper-right-hand area of FIG. 3 is an overhead view of the guide insert 60, and shown in the lower-left-hand portion of FIG. 3 is a longitudinal section of the guide insert 60. The sectional plane of the section in the lower-left-hand area corresponds to the sectional plane of FIG. 2.

The guide insert 60 is depicted in FIG. 3 in an unbent or straight form, in which it is for instance produced. The guide insert 60 is formed, for instance, of polyetheretherketone (PEEK, an aromatic, partly crystallized thermoplast of the group of polyaryletherketones) or another polyaryletherketone (PAEK) or another thermoplast or PTFE (also known under its market name of Teflon) or another elastic material.

The guide insert 60 comprises, alternating in the longitudinal direction, the support sections 62 and flexible sections 64 already described above with reference to FIG. 2. The support sections 62 have a cross-section that is adapted to the cross-section of a hollow space in the shaft 30, so that the support sections 62 are guided transversally with little or no free play in the shaft 30 or are even elastically clamped in place there. The flexible sections 64 have a smaller or essentially smaller cross-section than the cross-sections of the support sections 62 and the cross-section of the hollow space in the shaft 30. The support sections 62, in addition, comprise flattened areas 67, which are described in more detail hereinafter with reference to FIG. 4. The channel 66 is entirely inside the cross-section of the support sections 62 of the guide inert 60 over the entire length of the guide insert 60.

Figure 4:
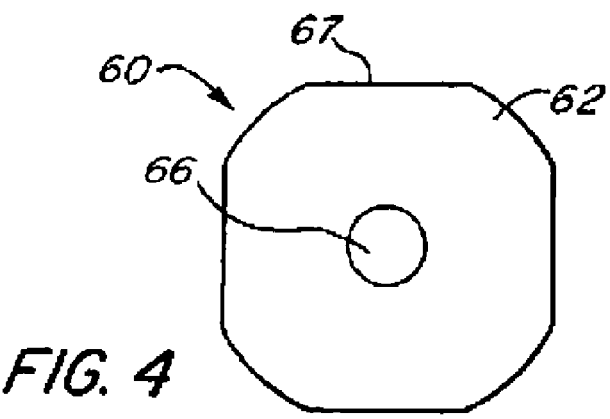
FIG. 4 is a schematic depiction of a cross-section of a guide insert.
Figure 5:
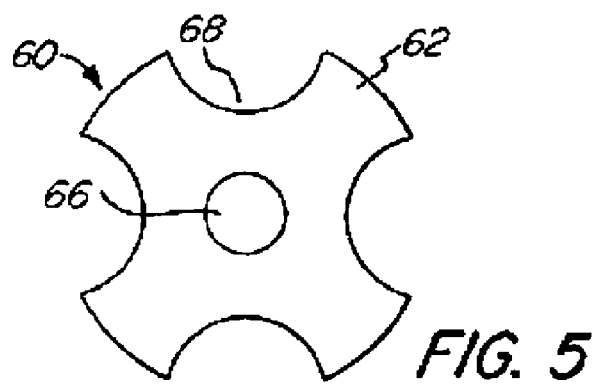
FIG. 5 is a schematic depiction of a cross-section of another guide insert.

FIGS. 4 and 5 present schematic depictions of cross-sections of support sections 62 of guide inserts 60 in similar manner as described above with reference to FIGS. 2 and 3. The sectional planes here are perpendicular to the longitudinal direction of the shaft 30 described above with reference to FIGS. 1 and 2 and of the transmission element 40 described with reference to FIGS. 1 and 2 and perpendicular to the visual planes of FIGS. 1 through 3.

FIG. 4 shows a cross-section of a support section 62 of a guide insert 60 that differs from a purely circular form because of the flattened areas 67. FIG. 5 shows a cross-section of a support section 62 of a guide insert 60 that differs from a purely circular form because of grooves 68. The flattened areas 67 or grooves 68 permit the flowing of an irrigation fluid, in particular of an irrigation liquid, in the longitudinal direction of the shaft between an interior wall of the shaft and the guide insert 60.

FIGS. 4 and 5 each show a regular arrangement of four flattened areas 67 or of four grooves 68. Rather than these, any other number of flattened areas 67 or of grooves 68 and an irregular arrangement of the flattened areas 67 or grooves 68 are also possible. The cross-section of the groove 68 can also differ from the depiction in FIG. 5. In particular, the cross-section of the groove 68 can take the form of a segment of a circle, a trapezoid, a rectangle, or any other form.

The channel 66 is shown in FIGS. 2 through 5 as concentric or coaxial in each case to the outer periphery of the guide insert 60 and to the tubular haft 30. Instead of this, an eccentric arrangement of the channel 66 is also possible. Contrary to the depictions in the illustrations, in addition, non-circular cross-sections of the shaft 30 and of the transmission element 40 are possible. In place of the alternating arrangement of support sections 62 and flexible sections 64 described and presented in the illustrations, a helical structure of the guide insert is also possible, for instance. In a helical structure of the guide insert 60, between one or more screw-shaped studs of the guide insert 60 that are contiguous with the interior wall of the hollow space in the shaft 30, there remains a corresponding number of screw-shaped channels, which permit the streaming or flowing of an irrigation fluid in the longitudinal direction of the shaft 30.

A guide insert 60, as described in the foregoing with reference to FIGS. 2 through 5, can be positioned only, as seen in FIG. 2, in a bent area of the shaft 30. While the transmission element 40 in any case advantageously comprises a constant cross-section within the guide insert 60 or is cylindrically symmetrical (translationally symmetrical to the longitudinal direction), in this case the transmission element 40 can comprise a different cross-section outside the guide insert 60. Alternatively the guide insert 60 can have a greater length and also can be positioned in straight sections of the shaft 30 or can extend over the entire length of the shaft 30. Unlike the depiction seen above with reference to FIGS. 2 through 5, the channel 66 in addition can alternatively be positioned only in sections inside or completely inside the cross-section of the guide insert 60. For example, the transmission element 60 can run only in the areas of the support sections 62 inside the support sections 62 of the guide insert 60 and in the flexible sections 64 outside the guide insert 60.

The invention claimed is:

1. A manipulator, comprising:
a shaft having a proximal end and a curved distal end, the distal end of the shaft having a manipulation device;
a transmission element positioned in the shaft for transmitting at least one of a force and a motion between the proximal end and the distal end of the shaft; and
a guide insert positioned in the shaft for guiding the transmission element, such that the transmission element is configured to slide with respect to the guide insert in a longitudinal direction of the shaft, the guide insert including alternating support sections and flexible sections in its longitudinal direction throughout the length of the shaft, the support sections having a cross-section that includes at least one flattened area or at least one groove, the flexible sections allowing for bending of the guide insert;
wherein at least part of the support sections are contiguous with an interior wall of the shaft, and whereby the flexible sections have cross-sections that are smaller than an internal cross-section of the shaft;
wherein irrigation openings are defined between the support sections and the interior wall of the shaft; and
wherein the irrigation openings permit an irrigation fluid to flow therethrough in the longitudinal direction of the shaft.

2. The manipulator of claim 1, wherein the guide insert comprises a channel in which the transmission element is slidably positioned.

3. The manipulator of claim 1, wherein the transmission element and the guide insert are composed of different materials.

4. The manipulator of claim 1, wherein a cross-section of the transmission element is constant between the proximal end and the distal end.

5. The manipulator of claim 1, wherein the manipulation device includes at least one of a forceps, a grip, a cutting tool, and a punching tool.

6. The manipulator of claim 1, wherein the manipulator is an endoscopic manipulator.

7. A guide insert for a manipulator with a shaft between a proximal end and a distal end, the guide insert comprising:
at least two support sections with a cross-section adapted to a hollow space of the shaft, the at least two support sections having a cross-section that includes at least one flattened area or at least one groove;
at least two flexible sections, the at least two flexible sections allowing for bending of the guide insert, the at least two support sections and the at least two flexible sections alternate in the longitudinal direction of the guide insert throughout the entire length of the shaft; and
a channel in which a transmission element is configured to be slidably positioned for transmitting at least one of a force and a motion between the proximal end and the distal end;
wherein at least part of the support sections are configured to be contiguous with an internal wall of the shaft, and wherein the flexible sections have cross-sections that are smaller than an internal cross-section of the shaft;

wherein irrigation openings are defined between the support sections and the internal wall of the shaft; and wherein the irrigation openings permit an irrigation fluid to flow therethrough in a longitudinal direction of the shaft.

8. The manipulator of claim 1, wherein the manipulator includes an arrangement of four flattened areas or of four grooves.

9. The manipulator of claim 1, wherein the irrigation openings are defined between the at least one flattened area or at least one groove in the support sections of the guide insert and the interior wall of the shaft.

10. The manipulator of claim 1, further comprising a handling device directly connected to the proximal end of the shaft, wherein the handling device includes a fixed gripping member, a connection element, a movable gripping member and a joint.

11. The manipulator of claim 10, wherein the fixed gripping member is rigidly connected with the connection element and a lever is rigidly connected with the movable gripping member.

12. The manipulator of claim 1, wherein the support sections are guided transversally with no free play in the shaft.

13. The manipulator of claim 1, wherein the support sections are elastically clamped in place within the shaft.

14. The manipulator of claim 1, wherein the transmission element has a different cross-section outside an area of the guide insert.

15. The manipulator of claim 10, wherein the transmission element extends out of the connection element.

16. The manipulator of claim 10, wherein the end of the transmission element is in a jointed coupling with the handling device.

17. The manipulator of claim 1, wherein the transmission element is a single transmission element.

18. The guide insert of claim 7, wherein the transmission element is a single transmission element.

19. The guide insert of claim 7, wherein the irrigation openings are defined between the at least one flattened area or at least one groove in the support sections of the guide insert and the internal wall of the shaft.

* * * * *